(12) United States Patent
Aghara et al.

(10) Patent No.: US 11,042,130 B2
(45) Date of Patent: Jun. 22, 2021

(54) AUTOMATIC ADJUSTMENT OF HEAD MOUNTED DISPLAY STRAPS

(71) Applicant: Intel Corporation, Santa Clara, CA (US)

(72) Inventors: Sanjay R. Aghara, Bangalore (IN); Ramesh Pendakur, Gaston, OR (US); Aditya K. Raut, Bangalore (IN); Nishant Kamat, Bangalore (IN); Sean J. Lawrence, Bangalore (IN)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 16/684,112

(22) Filed: Nov. 14, 2019

(65) Prior Publication Data

US 2020/0150597 A1 May 14, 2020

Related U.S. Application Data

(63) Continuation of application No. 15/233,795, filed on Aug. 10, 2016, now Pat. No. 10,488,830.

(51) Int. Cl.
*G05B 13/02* (2006.01)
*A61B 5/00* (2006.01)
(Continued)

(52) U.S. Cl.
CPC .......... *G05B 13/021* (2013.01); *A61B 5/1172* (2013.01); *A61B 5/6803* (2013.01);
(Continued)

(58) Field of Classification Search
CPC ... G05B 13/021; A61B 5/6803; A61B 5/6843; A61B 5/1172; A61B 5/6831; G02B 27/017; G06F 3/012
See application file for complete search history.

(56) References Cited

U.S. PATENT DOCUMENTS

| 5,682,172 A | 10/1997 | Travers et al. |
| 8,276,588 B1 | 10/2012 | Connor |

(Continued)

FOREIGN PATENT DOCUMENTS

WO 2015196255 12/2015

OTHER PUBLICATIONS

International Searching Authority, "International Search Report and Written Opinion," issued in connection with International Patent Application No. PCT/US2017/042869, dated Oct. 20, 2017, 11 pages.

(Continued)

*Primary Examiner* — Daniel Cavallari
(74) *Attorney, Agent, or Firm* — Hanley, Flight & Zimmerman, LLC

(57) ABSTRACT

Embodiments are generally directed to automatic adjustment of head mounted display straps. An embodiment of a head mounted display apparatus includes a display unit; a strap harness including one or more straps; one or more pressure sensors; a microcontroller; and one or more automatic adjustment mechanisms for the one or more straps, wherein the microcontroller is to adjust the one or more straps by controlling operation of the one or more automatic adjustment mechanisms based at least in part on sensor data from the one or more pressure sensors.

20 Claims, 10 Drawing Sheets

(51) Int. Cl.
*A61B 5/1172* (2016.01)
*G02B 27/01* (2006.01)
*G06F 3/01* (2006.01)

(52) U.S. Cl.
CPC .......... *A61B 5/6843* (2013.01); *G02B 27/017* (2013.01); *G06F 3/012* (2013.01); *A61B 5/6831* (2013.01)

(56) References Cited

U.S. PATENT DOCUMENTS

| | | | |
|---|---|---|---|
| 8,947,195 B1 | 2/2015 | Anvari | |
| 9,274,340 B2 | 3/2016 | Lyons | |
| 10,212,517 B1* | 2/2019 | Beltran | H04S 3/004 |
| 10,359,806 B2* | 7/2019 | Osman | A63F 13/25 |
| 10,488,830 B2 | 11/2019 | Aghara et al. | |
| 2014/0098009 A1 | 4/2014 | Prest et al. | |
| 2014/0152531 A1 | 6/2014 | Murray et al. | |
| 2015/0224275 A1 | 8/2015 | Pastoor et al. | |
| 2016/0140764 A1 | 5/2016 | Bickerstaff et al. | |
| 2016/0259986 A1 | 9/2016 | Yun et al. | |
| 2016/0361512 A1* | 12/2016 | Lawrenson | A61M 16/0605 |
| 2017/0277254 A1 | 9/2017 | Osman | |
| 2018/0046147 A1 | 2/2018 | Aghara et al. | |

OTHER PUBLICATIONS

International Searching Authority, "International Preliminary Report on Patentability," issued in connection with International Patent Application No. PCT/US2017/042869, dated Feb. 21, 2019, 10 pages.

United States Patent and Trademark Office, "Non-Final Office Action," issued in connection with U.S. Appl. No. 15/233,795, dated Apr. 6, 2018, 20 pages.

United States Patent and Trademark Office, "Final Office Action," issued in connection with U.S. Appl. No. 15/233,795, dated Mar. 19, 2019, 39 pages.

United States Patent and Trademark Office, "Notice of Allowance and Fee(s) Due," issued in connection with U.S. Appl. No. 15/233,795, dated Aug. 1, 2019, 28 pages.

* cited by examiner

AUTOMATIC ADJUSTMENT OF HEAD MOUNTED DISPLAY STRAPS

RELATED APPLICATION

The present application is a continuation of and claims the benefit of U.S. patent application Ser. No. 15/233,795, filed on Aug. 10, 2016 and entitled "AUTOMATIC ADJUSTMENT OF HEAD MOUNTED DISPLAY STRAPS", which which is incorporated by reference in its entirety.

TECHNICAL FIELD

Embodiments described herein generally relate to the field of electronic devices and, more particularly, automatic adjustment of head mounted display straps.

BACKGROUND

Head Mounted Display (HMD) usage is rapidly expanding with the advances in virtual reality and related technology. HMD devices will be utilized by a new audience as the expansion in potential uses progresses.

In order to make use of this technology, any user, including a new or infrequent user, is required to wear an HMD, which has certain difficulties. Because of the weight and balance of an HMD, and because a properly fitting HMD is necessary to a positive user experience, properly adjusted HMD straps play a big role in comfort.

However, users find it cumbersome to adjust straps every time they wear the HMD device, which is a significant issue when multiple users share the same HMD. If straps are not properly fitted on the user's head, the wearing of an HMD will quickly become uncomfortable for a user, which can greatly offset the advantages the technology can provide.

BRIEF DESCRIPTION OF THE DRAWINGS

Embodiments described here are illustrated by way of example, and not by way of limitation, in the figures of the accompanying drawings in which like reference numerals refer to similar elements.

DETAILED DESCRIPTION

Figure 1:
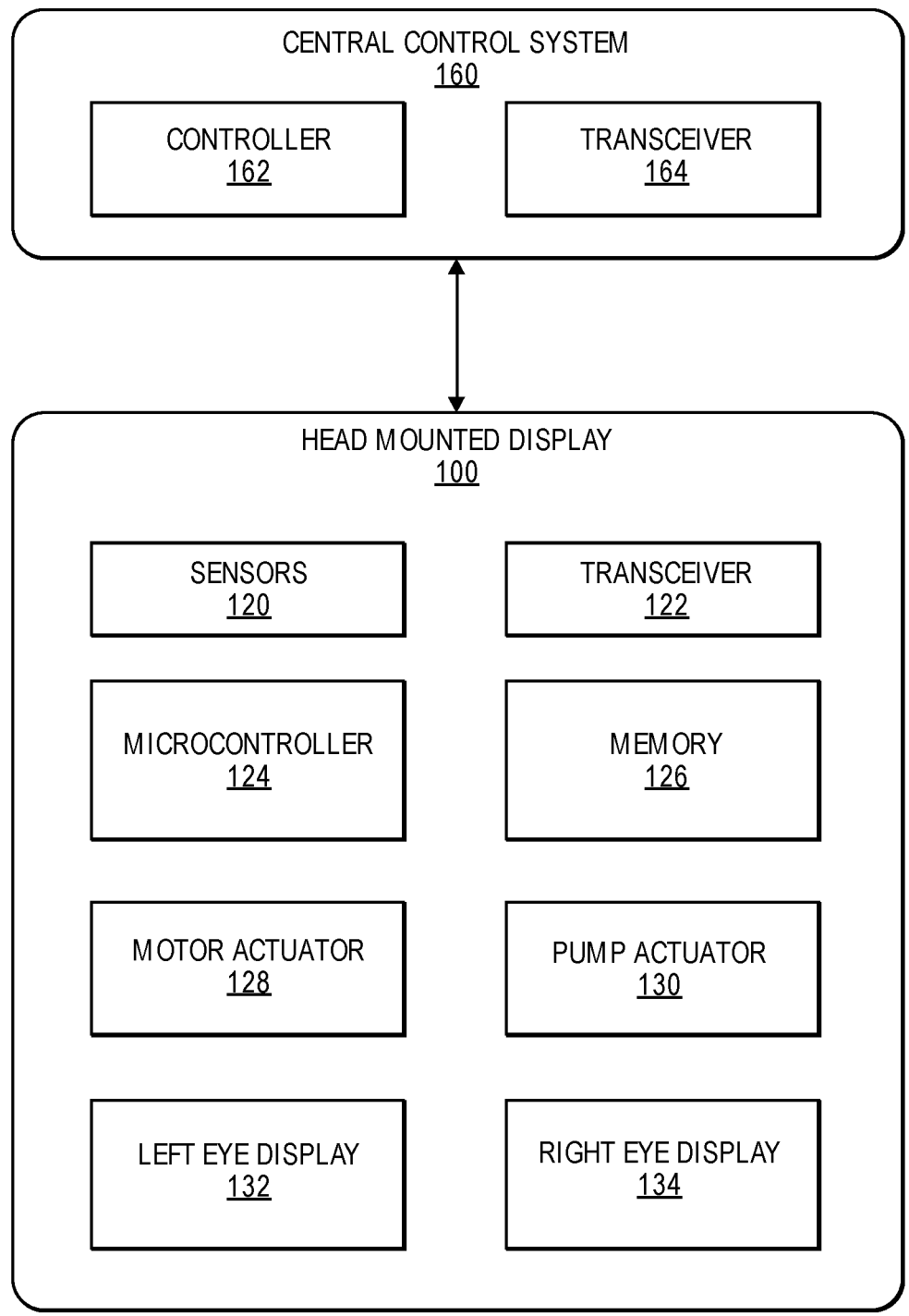
FIG. 1 is an illustration of components of a head mounted display according to an embodiment.

Embodiments described herein are generally directed to automatic adjustment of head mounted display straps.

For the purposes of this description:

"Head mounted display" or "HMD" refers to a display device worn on the head of a user, the head mounted display including a display optic in front of either or both eyes of the user. A hand mounted display may include one or more straps to support the unit on the user's head.

For viewing operations, HMDs, which have the advantage of an immersive visual experience for a user, are significantly larger and heavier than eyeglass units (spectacles), and hence HMDs require straps to hold the units in place. Further, the weight of the HMD is generally distributed with more weight towards the front of the unit.

When a user wears an HMD and the straps of the HMD unit (wherein the straps together may be referred to as a harness or strap harness) are not adjusted properly to snugly fit a user's head, the weight distribution of the HMD will become unbalanced and the wearing of the HMD will quickly become uncomfortable for the user.

For a conventional HMD unit, it is necessary for the user to adjust the straps for proper fit to the user's face and head. As multiple users may utilize a single HMD unit, and with a population of users who may have a great deal of variation in head size and shape, there may be a large amount of adjustment needed to properly fit an HMD unit.

Further, the usage of an HMD generally utilizes the movement of the user's head in the display process, with the display following the head movement in order to provide data in relation to the point of view of the user. However, this movement can loosen the straps over time, thus creating a circumstance in which a user is required to readjust the straps during usage or pause usage to address the problem, and thereby further distract from the intended usage experience.

In some embodiments, a head mounted display unit include one or more automatically adjusting straps that adjust the straps for a particular user, such as adjusting the strap tension, position, or other strap setting for a user. In some embodiments, a device or system provides for automatic adjustment of one or more straps of an HMD prior to usage, during usage, or both. The adjustment of the strap may include changing a strap tension (which may generally be referred to as tightening or loosening the straps, or shortening or lengthening the straps). The adjustment of the straps may also include inflating or deflating the straps or otherwise changing a shape of the straps. However, embodiments are not limited to these options, and may include other means of changing the fit of the straps of an HMD harness.

In some embodiments, an apparatus, system, or process provides for automatic adjustment of straps for a user based on pressure. In some embodiments, a HMD includes one or more sensors to measure pressure of one or more portions of the HMD on the face or head of the user. In some embodiments, an apparatus, system, or process provides for detecting pressure at points where the straps or other portion of the HMD are in direct contact with the user. In some embodiments, different measurements may be used, such a measurement of a tension of a strap, a measurement of a balance of a strap, a measurement of light entering the HMD (indicating a gap caused by an improper fit), or other measures of the physical relation.

In an particular implementation, an HMD includes one or more pressure sensors to detect pressure on face and head points (such as the nose, forehead, upper cheek, or other points, or any combination of such points), and the HMD and auto-adjust the straps of the HMD to provide a proper fit of the HMD for the particular individual who is using In some embodiments, an HMD includes one or more automatic adjustment mechanisms for adjustment of the straps of the HMD. In some embodiments, the one or more automatic adjustment mechanisms using a motor rolling mechanism, wherein the rolling mechanism is operable to tighten or loosen one or more straps of the shorten or lengthen the length of the attaching straps.

In some embodiments, an HMD includes pressure sensors on the straps of the harness, the pressure sensors facing the user's head, the straps being inflatable straps that can be inflated or deflated based on the pressure detected on the straps to adjust the straps to provide a correct snug fit with user's head.

In some embodiments, if a user is not comfortable after the auto adjustment, the user can manually fine tune strap adjustment.

In some embodiments, an HMD system includes stored or pre-loaded profile information for a particular user, wherein such profile may be stored in and accessed from local or remote (cloud) storage. In some embodiments, the HMD straps can be adjusted to profile settings upon the user being recognized by the system. In some embodiments, the system includes a biometric sensor (such as a fingerprint scanning, IRIS scanning, or other scanning device) integrated into HMD, and wherein, upon a user being identified based on input biometric data via the biometric sensor the user's unique profile with strap fitment data may be loaded from the local or cloud storage, and automatically implemented.

In some embodiments, a process for automatic HMD adjustment includes some or all of the following:

(1) Receive sensor feedback and automatically adjust HMD straps based on the sensor data, which may include either or both of the following:

(a) Receive feedback for points where HMD touches user's face utilizing pressure sensors on HMD that detect pressure at these face points, and apply motor rolling strap mechanism to adjust the straps accordingly based on pressure data.

(b) Receive sensor from feedback inflatable straps as feedback by reading pressure sensors on straps (on the side of the strap facing the user's head facing side) and inflating straps with air pressure beneath strap layer till straps snuggly fit the user's head.

(2) After auto-adjustment of straps, such as per process (a), process (b), or both, the user then is free to fine tune adjustment manually for a final adjustment. In some embodiments, by having biometric sensor integrated into the HMD, this final adjustment can be stored in user's profile which can be used for auto strap adjustment when the same user uses the HMD again.

(3) Once straps are auto adjusted and during the course of usage of HMD, readjust the straps periodically if the fitting changes, such as a result of the user's head movement.

FIG. 1 is an illustration of components of a head mounted display according to an embodiment. In some embodiments, an HMD 100 includes one or more sensors 120 to detect indications of pressure on the face or head of the user of the HMD. In some embodiments, the HMD 100 includes a microcontroller 124 to control operations of the HMD 100, wherein control may include, but is not limited to, automatic control of straps of the HMD to adjust a fit of the straps for a user; a memory 126, wherein the memory 126 may include data concerning a fit of the straps of the HMD 100 for a particular user; and one or more of a motor actuator 128 or pump actuator 130 to adjust the straps of the HMD.

In some embodiments, the HMD 100 further includes one or more displays for the user of the user wearing the HMD, wherein the displays may include a left eye display 132 and a right eye display 134; and a wired or wireless transceiver for communication with one or more external devices, wherein the external device may include a central control system 160.

In some embodiments, elements of the central control system 160 may include, but are not limited to, a controller 162 for control operations that may include control of certain elements of the HMD 100, and a wired or wireless transceiver 164 for communication with the HMD 100, including transmission of commands to the HMD 100. In some embodiments, a function of the controller 162 may include control of at least a portion of the automatic control of the straps of the HMD 100.

Figure 2:
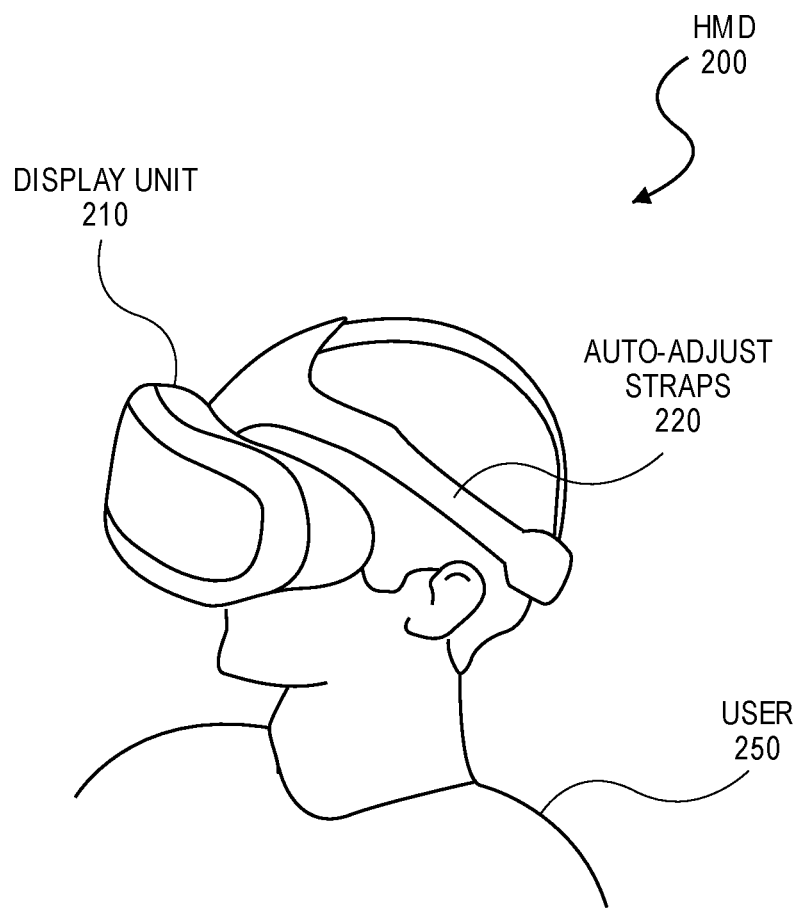
FIG. 2 is an illustration of a user utilizing an HMD with automatic strap adjustment.

FIG. 2 is an illustration of a user utilizing an HMD with automatic strap adjustment. In some embodiments, an HMD 200 includes a display unit 210 and one or more automatically adjusting straps 220. In some embodiments, the HMD 200 may include the components illustrated in FIG. 1. In some embodiments, the HMD 200 is to perform automatic adjustment of the straps 220 to properly fit the face and head of a particular user 250. In some embodiments, the automatic adjustment may occur at one or more times during the use of the HMD 200 by the user 250.

In some embodiments, the automatic adjustment of the straps 220 is based at least in part on signals produced by one or more sensors, wherein the sensors may include the measurement of pressure on the face or head of the user 250 at one or more points. Sensors may include pressure sensors 315 as illustrated in FIG. 3 or pressure sensors 540 as illustrated in FIG. 5A.

Figure 4A:
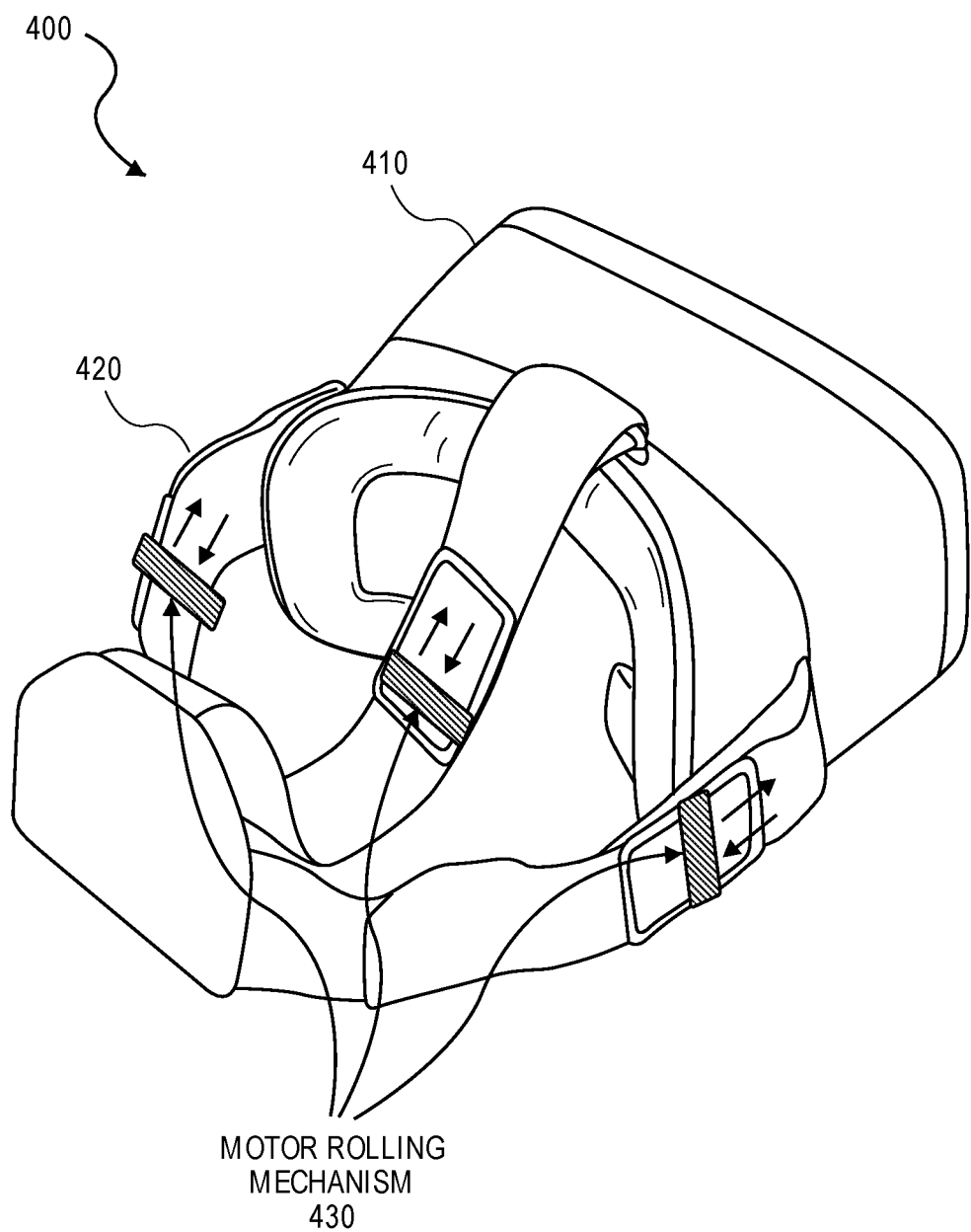
FIG. 4A is an illustration of a first implementation of a head mounted display with motor rolling mechanism to provide automatic strap adjustment according to an embodiment.
Figure 4B:
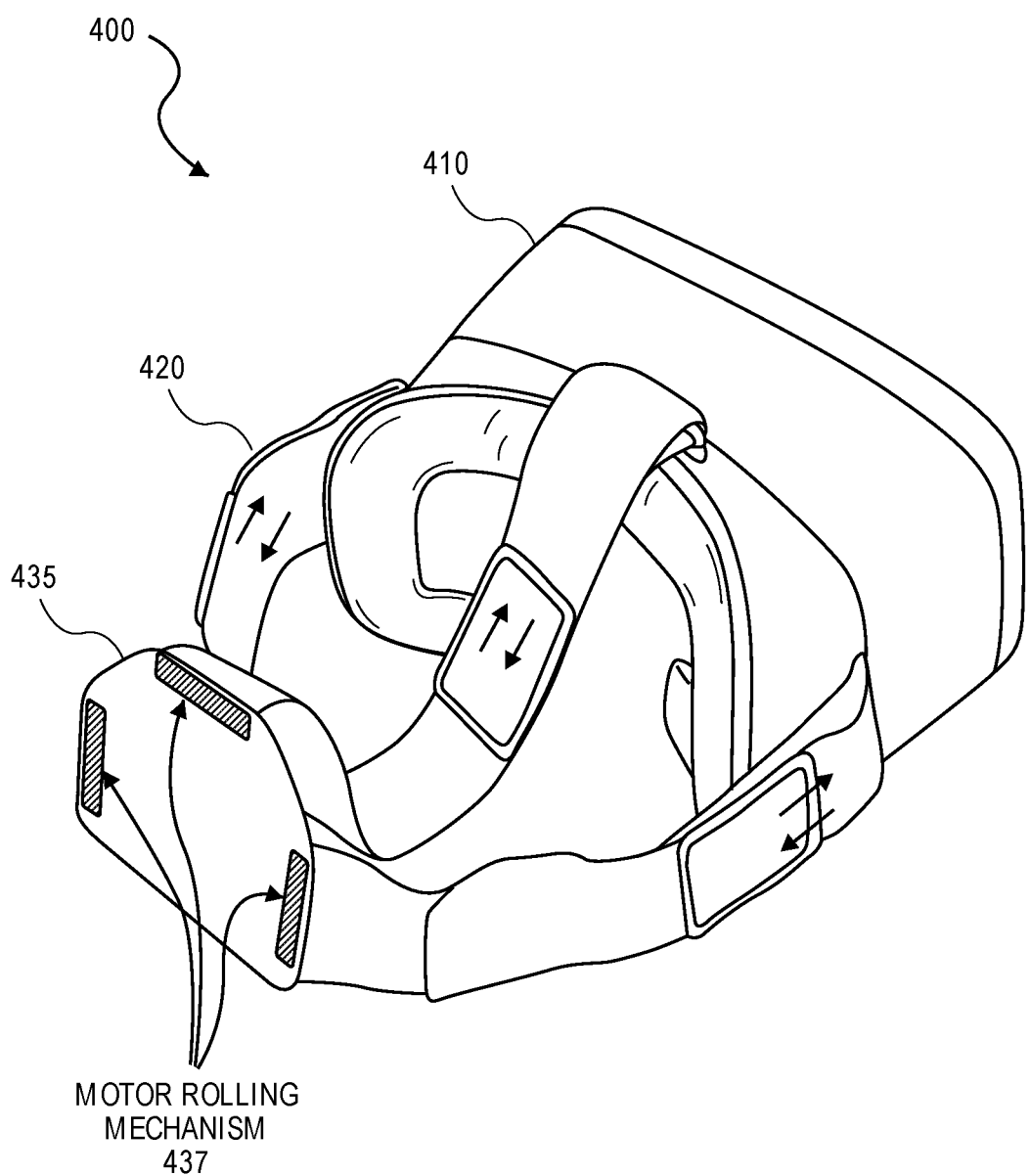
FIG. 4B is an illustration of a second implementation of a head mounted display with motor rolling mechanism to provide automatic strap adjustment according to an embodiment.
Figure 5A:
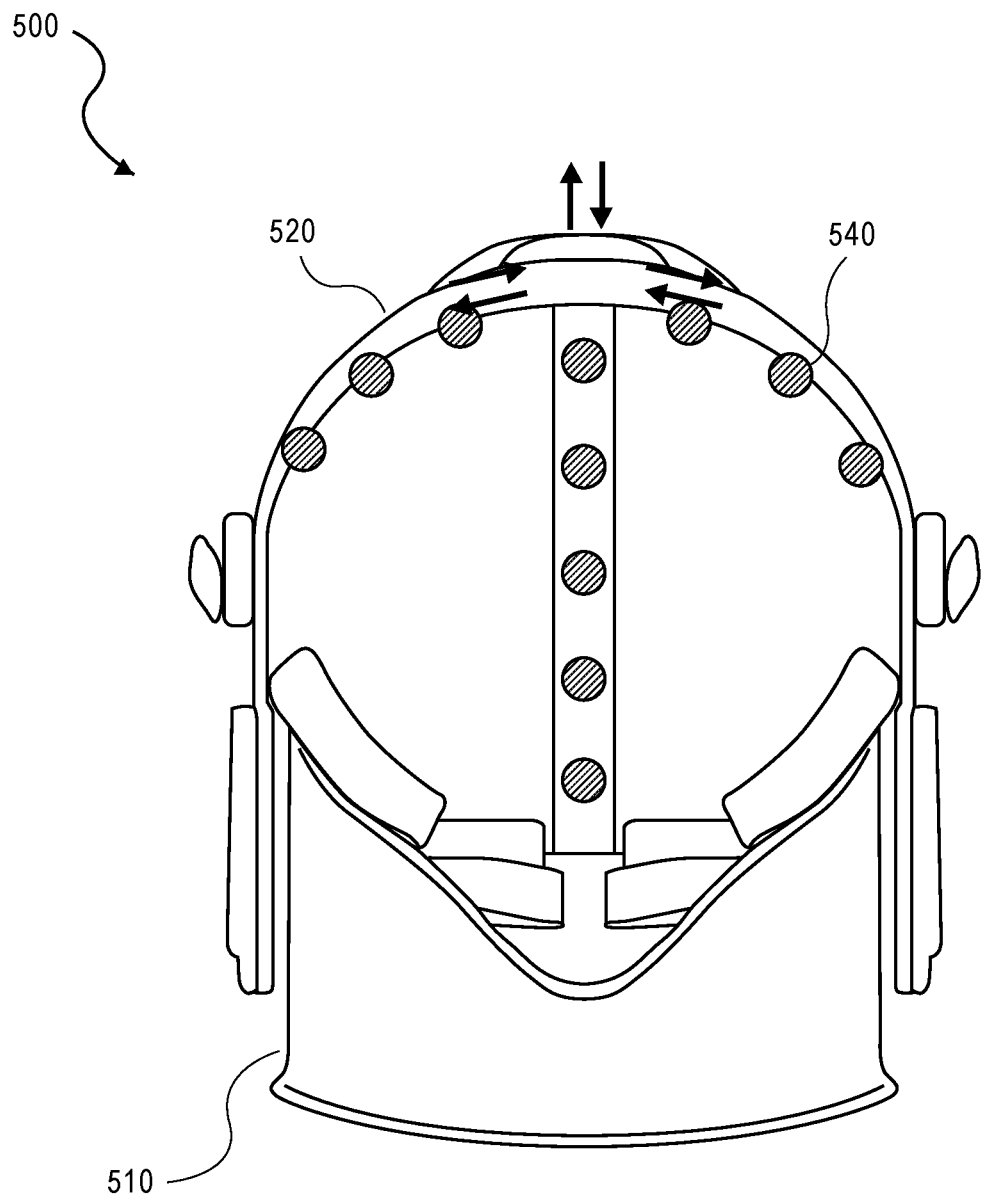
FIG. 5A is an illustration of a first view of a head mounted display with strap inflation to provide automatic strap adjustment according to an embodiment.
Figure 5B:
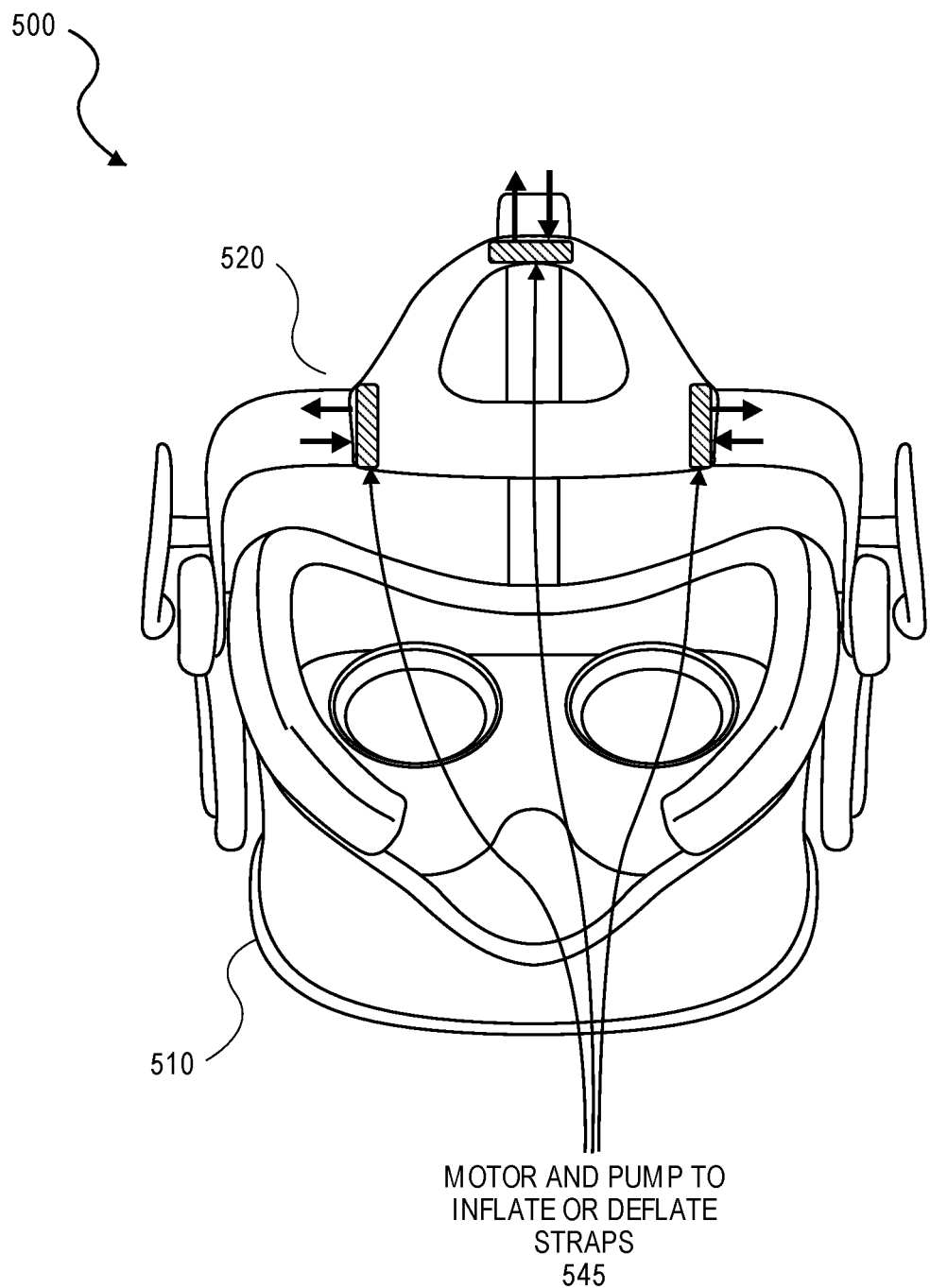
FIG. 5B is an illustration of a second view of a head mounted display with strap inflation to provide automatic strap adjustment according to an embodiment.

In some embodiments, the automatic adjustment of the straps 220 may include the activation of one or more motor rolling mechanisms 430 and 437 as illustrated in FIGS. 4A and 4B; one or more inflatable straps of a strap harness 520 as illustrated in FIGS. 5A and 5B; other strap adjustment mechanisms to adjust a size or shape of the straps 220; or a combination of strap adjustment mechanisms.

Figure 6A:
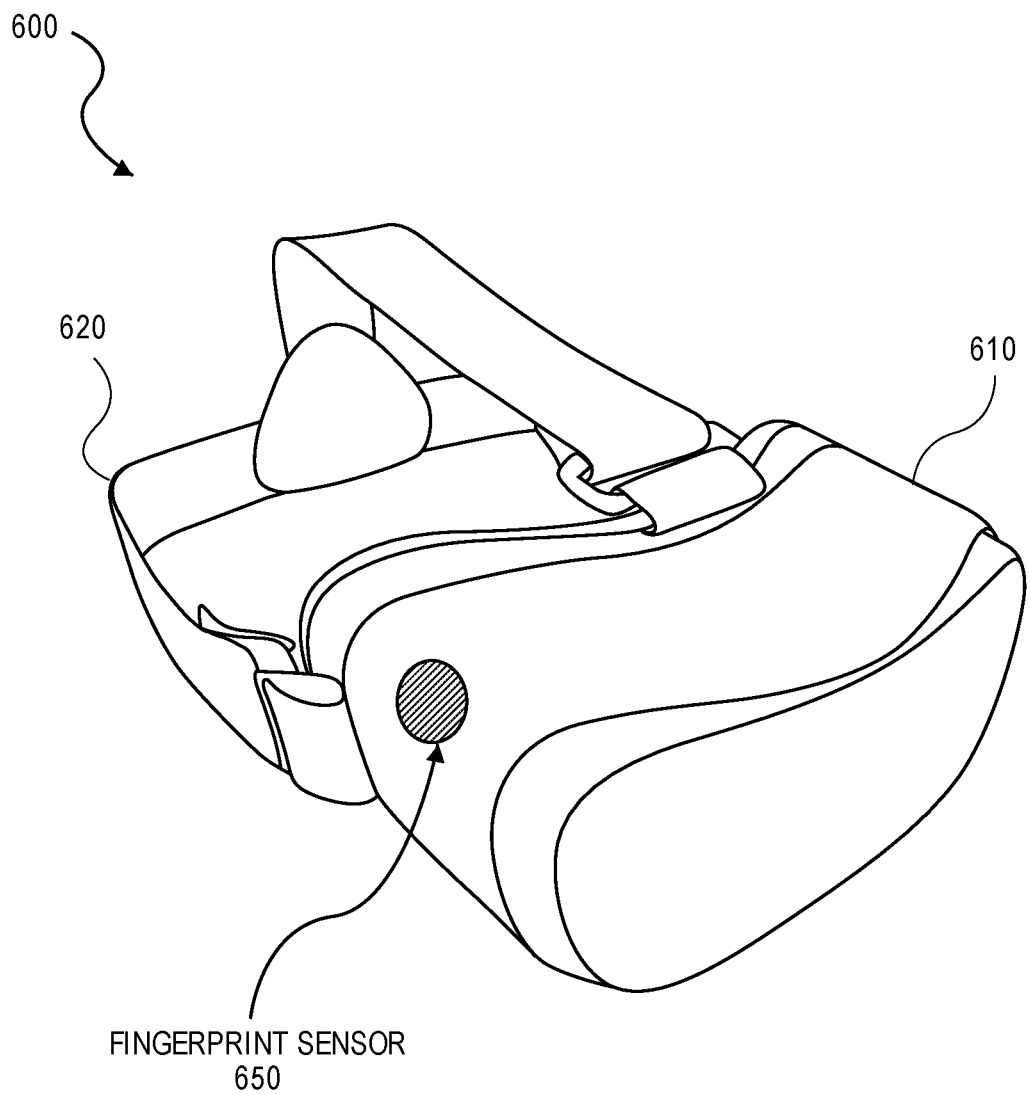
FIG. 6A is an illustration of a head mounted display with fingerprint biometric sensing to provide automatic strap adjustment according to an embodiment.
Figure 6B:
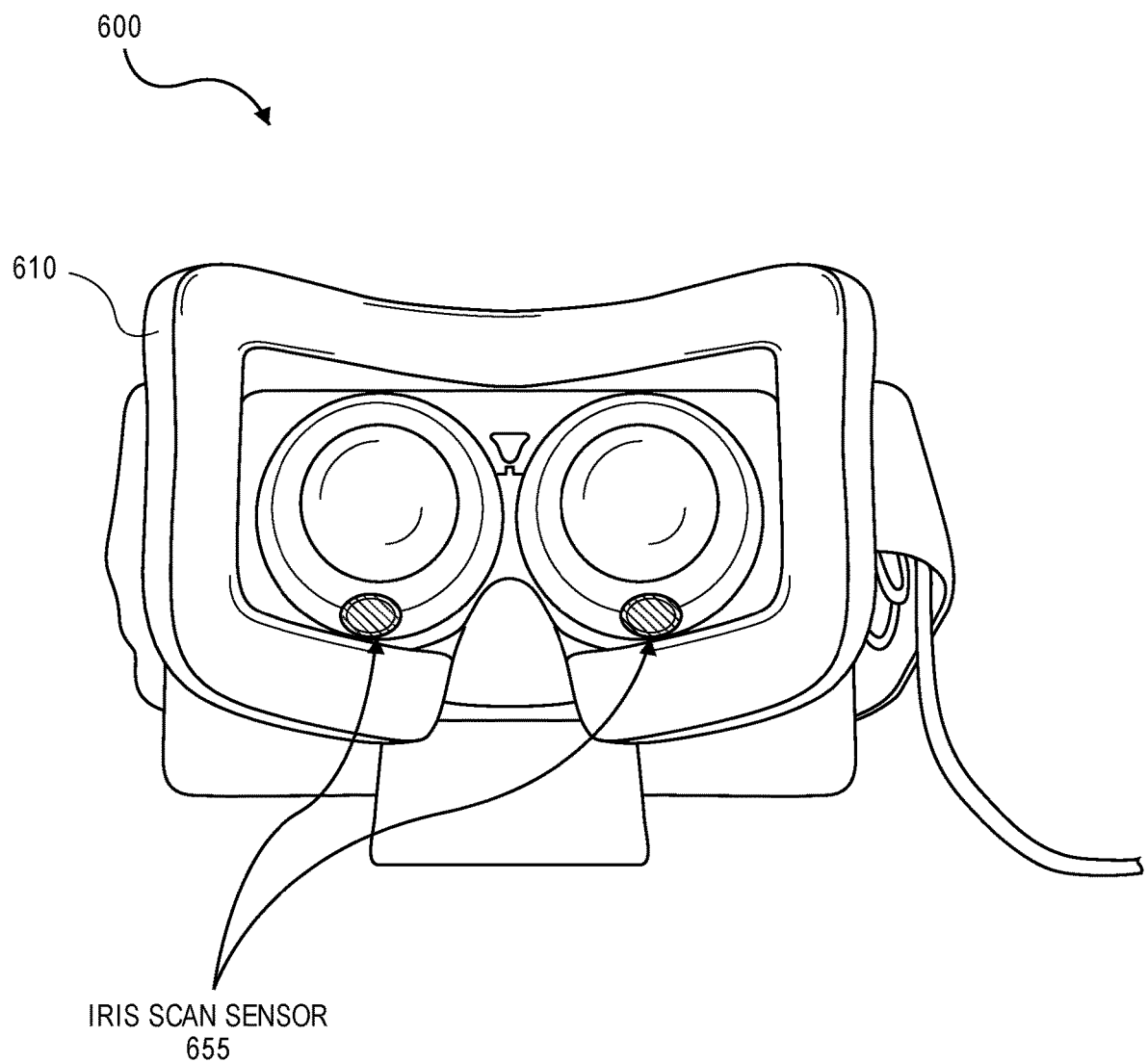
FIG. 6B is an illustration of a head mounted display with iris scanning biometric sensing to provide automatic strap adjustment according to an embodiment.

In some embodiments, the automatic adjustment of the straps 220 includes the application of fitting data for the particular user 250. In some embodiments, an HMD may automatically adjust the straps 220 upon recognizing the user 250 based at least in part on sensing of biometric data, wherein the input of biometric data may include, but is not limited to, the sensing of fingerprint data from a finger of the user 250 utilizing a fingerprint sensor 650 as illustrated in FIG. 6A or the sensing of iris data from one or both eyes of the user 250 utilizing an iris scan sensor 655 as illustrated in FIG. 6B.

Figure 3:
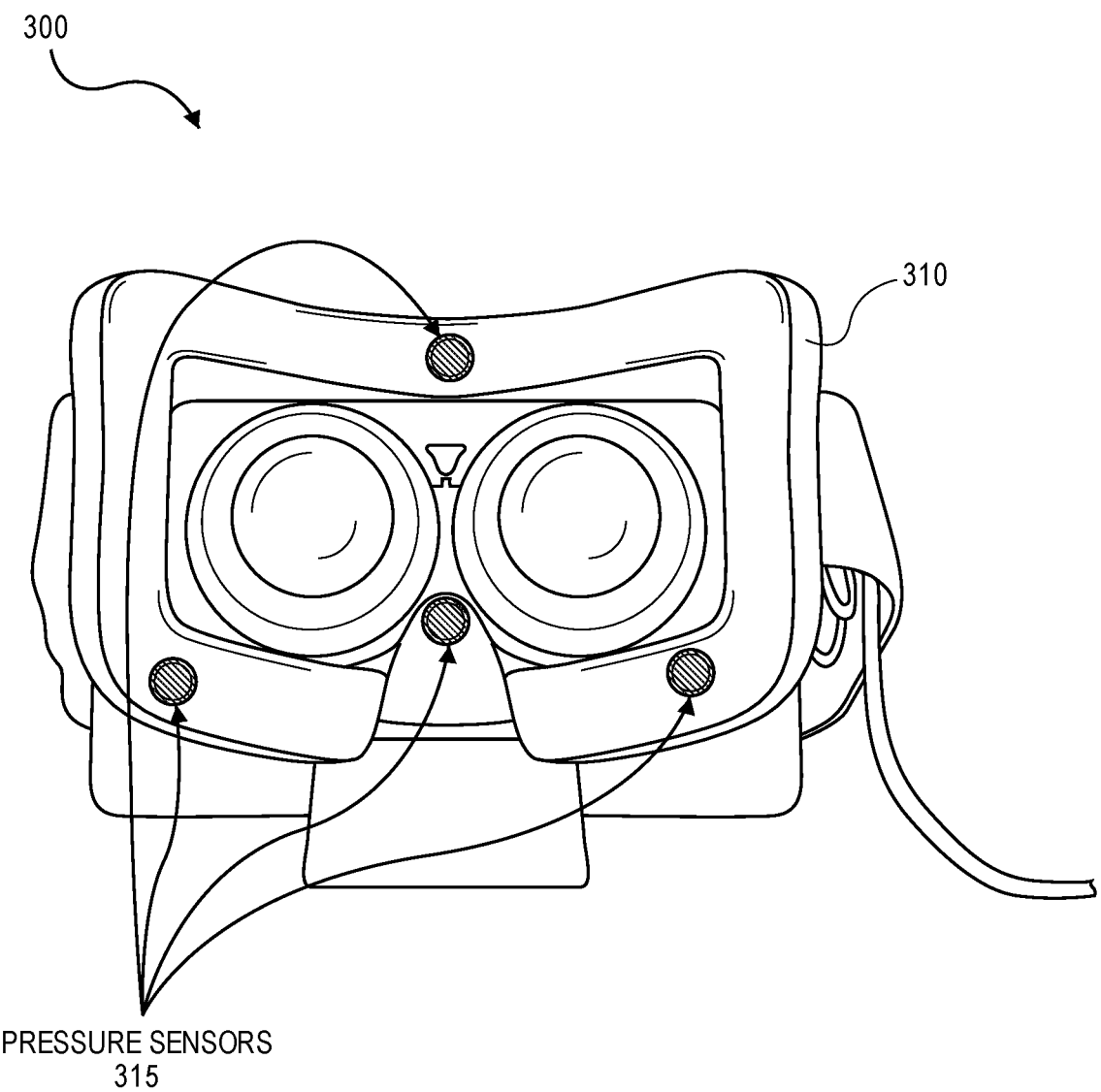
FIG. 3 is an illustration of pressure sensors of a head mounted display with automatic strap adjustment according to an embodiment.

FIG. 3 is an illustration of pressure sensors of a head mounted display with automatic strap adjustment according to an embodiment. In some embodiments, and HMD 300 includes a display portion 310, wherein the display portion 310 may include one or more pressure sensors 315 or other sensors to detect a pressure of contact of the HMD at one or more points on the face or head of a user. In some embodiments, the HMD 300 is to provide automatic adjustment of the straps of the HMD based at least in part on signals from the one or more sensors. FIG. 3 illustrates a particular example for the location of the pressures sensors of the HMD, but embodiments are not limited to this implementation, and may include different or additional pressure sensors to provide a fine-tuned adjustment of the HMD straps and to give best comfort fit for the user.

In some embodiments, a microcontroller of the HMD 300, such as microcontroller 124 as illustrated in FIG. 1, is to provide control signals to one or more strap adjustment mechanisms to provide for performance of the adjustment, which may include, but is not limited to, control signals to one or more motor rolling mechanisms 430 or 437 as illustrated in FIGS. 4A and 4B, or one or more pump mechanisms 545 as illustrated in FIG. 5B.

FIG. 4A is an illustration of a first implementation of a head mounted display with motor rolling mechanism to provide automatic strap adjustment according to an embodiment. In some embodiments, an HMD 400 includes a display unit 410 and one or more straps in a strap harness 420. In some embodiments, at least one of the straps in the harness 420 includes a motor rolling mechanism 430, wherein each motor rolling mechanism 430 is to automatically adjust a tension of a respective strap or straps of the harness 420. FIG. 4A illustrates a possible implementation, with a placement of a set of motor rolling mechanisms.

In some embodiments, the motor rolling mechanisms include motors that provide for the increase and decrease in tension. In some embodiments, the motors are connected to a microcontroller, such as microcontroller 124 illustrated in FIG. 1, wherein the microcontroller is to control the operation of the motors. In some embodiments, the microcontroller is to control these motors based on pressure sensor readings received by the microcontroller, wherein the pressure sensor readings may be from pressure sensors 315 such as illustrated in FIG. 3.

In an example, if pressure detected on a nose area is higher than a certain threshold value, an upper strap may need to be pulled in to reduce the pressure on the user's nose. In some embodiments, an upper strap motor is to be activated or triggered by the microcontroller to begin rolling the strap until the pressure on the nose area as indicated by the pressure sensor meets the respective threshold.

In a second example, if a pressure detected on a forehead area of the user is higher than a threshold while pressure detected on the nose area is below threshold, the upper strap motor will be triggered by the microcontroller to release the strap from the roller until forehead area pressure meets the threshold. Similarly, side straps may be adjusted based on pressure detected on an upper cheek area along with forehead and nose area.

FIG. 4B is an illustration of a second implementation of a head mounted display with motor rolling mechanism to provide automatic strap adjustment according to an embodiment. As illustrated, the HMD 400 again includes the display unit 410 and one or more straps in a strap harness 420. In some embodiments, a portion of the harness is a strap joint 435 (such as the rear strap joint illustrated in FIG. 4B) wherein multiple straps are joined. In some embodiments, the strap joint 435 includes one or more motor rolling mechanisms 437, wherein each motor rolling mechanism 437 is to automatically adjust a tension of a respective strap or straps of the harness 420.

FIG. 5A is an illustration of a first view of a head mounted display with strap inflation to provide automatic strap adjustment according to an embodiment. In some embodiments, an HMD 500 includes a display unit 510 and one or more straps in a strap harness 520. In some embodiments, at least one of the straps in the strap harness 520 is inflatable to provide automatic strap adjustment. In some embodiments, one or more straps of the strap harness 520 include one or more pressure sensors 540, the pressure sensors being on a side of the strap facing the head of the head of the user.

FIG. 5B is an illustration of a second view of a head mounted display with strap inflation to provide automatic strap adjustment according to an embodiment. In some embodiments, an HMD 500 includes a display unit 510 and one or more inflatable straps in a strap harness 520. In some embodiments, the HMD 500 includes one or more pump mechanisms 545, such as the motors and pumps illustrated in FIG. 5B, in the strap harness 520 to inflate the one or more inflatable straps to provide automatic strap adjustment.

In some embodiments, the inflatable straps of the harness are inflated or deflated based on pressure detected on straps with respect to user's head, such as using pressure signal data from the pressure sensors 540 illustrated in FIG. 5A. In some embodiments, the pump mechanism 545 is to pump air flow into straps for inflating straps if the pressure data indicates that additional pressure is needed. Similarly the pump mechanism is to deflate straps if the pressure reading is high on pressure sensor array.

In a particular implementation, to put on an HMD with inflatable straps, a user would first press a button to deflate and loosen all the straps (is not already done). The user would then place the HMD on the head, hold the eye piece in place, and then press a button to inflate all the straps such that the HMD fits snugly based on pressure sensor data. In some embodiments, a microcontroller in the HMD, such as microcontroller 124 illustrated in FIG. 1, will monitor the pressure sensor data to set pressure settings and provide a proper and comfortable fit for the HMD. In some embodiments, when removing the HMD, the user would again press the button (or press a second button) to deflate and loosen the straps for removal of the HMD.

In an example, when a user puts on the HMD initially, only a top strap will have pressure in the middle of the strap to support the load of the unadjusted HMD top of the user's head. Microcontroller monitoring of the sensor data provided by pressure sensors to first command a top strap pump mechanism to start inflating one or more top straps until pressure data from all top strap pressure sensors reach a certain first threshold. This state would give initial snug fit to the user and holds the HMD on the user's head. Once the one or more top straps are inflated and a snug fit provided, one or more side straps may also be inflated until pressure on the side straps reaches a certain second threshold, wherein the second threshold may be different than the first threshold. The adjusted side straps will hold the HMD firmly on user's head. Further, based on a user's head position there may be need to deflate one or more straps for comfort.

In some embodiments, a second pressing of a button or a pressing of a second button may cause the HMD microcontroller to provide commands to deflate straps completely and loosen up the fit of the HMD unit when the user wants to remove the HMD, thus assisting in ease of removal of the HMD and providing an additional comfort factor for the user.

FIG. 6A is an illustration of a head mounted display with fingerprint biometric sensing to provide automatic strap adjustment according to an embodiment. In some embodiments, an HMD 600 includes a display unit 610 and one or more straps in a strap harness 620. In some embodiments, the HMD 600 further includes a biometric sensor to identify a user. In some embodiments, the biometric sensor includes a fingerprint sensor 650, wherein the HMD may identify the user when the user places s finger on the fingerprint sensor 650, the sensor to record an image of the fingerprint of the user for identification.

FIG. 6B is an illustration of a head mounted display with iris scanning biometric sensing to provide automatic strap adjustment according to an embodiment. In some embodiments, an HMD 600 includes a display unit 610 and one or more straps in a strap harness 620. In some embodiments, the HMD 600 further includes a biometric sensor to identify a user, wherein the biometric sensor includes an iris scan sensor 655, wherein the HMD may identify the user when the user looks into the HMD, the iris scan sensor to record an image of the iris of an eye of the user for identification.

In some embodiments, an HMD 600 with biometric sensor 650-655 is to store details of a user's preferred strap fitting with the user's profile and use such data a next time the same user puts on HMD. In some embodiments, is order to enhance user experience, once the user wears the HMD and the straps are automatically adjusted based on pressure detected on face points, user can do a manual final adjustment and the final adjustment will be saved with the particular user's profile based on the user's identify that is recognized via a through biometric sensor in HMD. In some embodiments, the collected biometric data may be used when the same user puts on the HMD, and, based on the biometric user identity, previously saved data will be fetched from database and the straps are adjusted accordingly.

In some embodiments, a biometric sensor on an HMD 600 can be fingerprint sensor, iris scan sensor, or other biometric sensor placed on the HMD at locations that are easily accessible to the user, such as a fingerprint sensor on a side of the display unit 610 of the HMD or iris scan sensors inside the display unit 610 below the lenses within the display unit.

In some embodiments, with an HMD having biometric sensors, apart from strap adjustment profile, there can be other user profile data that can be stored and loaded based on user identification, such as (1) IPD (Interpupillary distance), including automatic adjustment of the distance between lens, displays, or bot to match the user's IPD; (2) Focus adjustment, including automatic adjustment of a distance between lens and display to correct the view based on user's eye prescription data; and (3) Any user specific data entered into user's profile, for use by different applications.

In some embodiments, strap tension may be can be adjusted based on user's usage matrix, which is built over a period of time based on content that user plays, user's head position through iris scan sensor and the amount of amount of motion of the HMD that is allowed. In some embodiments, an apparatus, system, or method includes the adjustable HMD straps being adjusted periodically if the fitting changes based on user's head movement.

HMDs commonly include an inertial measurement unit (IMU) sensor that is used for head tracking input, which is one of the primary means of user interaction. However, because of the head movements the strap fittings is likely to change. In some embodiments, an HMD is to check the pressure sensor data along with the motion data via the IMU data periodically or in real time to readjust the straps in real time. In some embodiments, automatic readjustment is implemented at certain intervals that are sufficiently spaced in order to so as to not affect the user experience by constant fitting adjustment.

Figure 7:
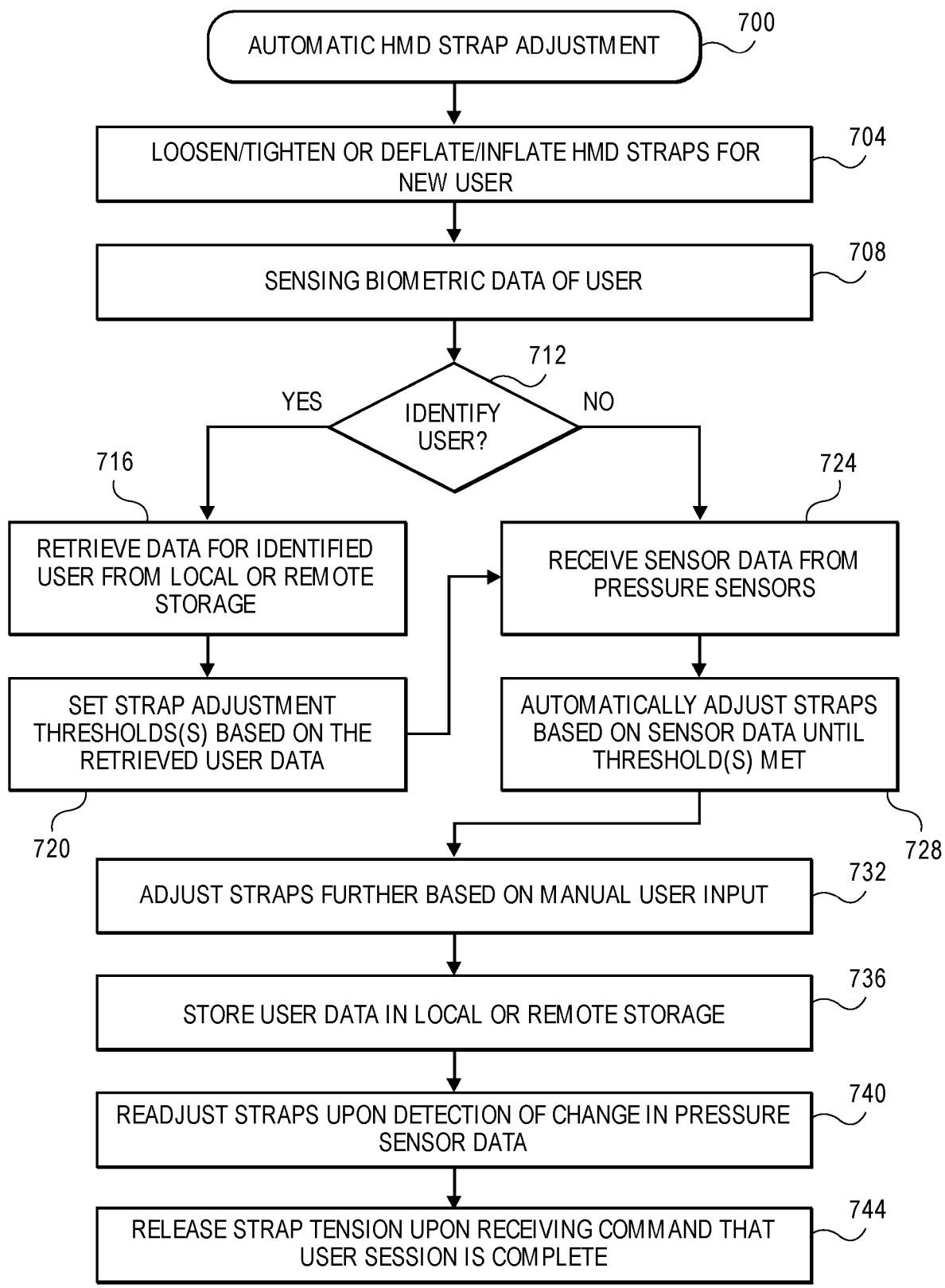
FIG. 7 is a flowchart to illustrate to illustrate a process for automatic head mounted display strap adjustment according to an embodiment.

FIG. 7 is a flowchart to illustrate to illustrate a process for automatic head mounted display strap adjustment according to an embodiment. In some embodiments, a process 700 may include the following:

704: Loosening or tightening, including deflating or inflating of an inflatable strap, the straps of a strap harness of an HMD for use of a new user. In some embodiments, the deflation or loosening of the straps may be in response to a prior user pressing a button to signal an end of use, or other operation to place the HMD straps in an initial loosened state. In some embodiments, the HMD straps may be partially tightened or inflated to an initial adjustment state. In some embodiments, initial adjustment of the HMD straps may be automatically initiated by detection of the user's presence, such as by detection by pressure sensors or proximity sensors within the HMD or by any other means. In some embodiments, the loosening/tightening or deflation/inflation of the straps of the HMD is in response to a microcontroller controlling operation of a motor rolling mechanism 430 as illustrated in FIG. 4A or 437 illustrated in FIG. 4B, or a pump mechanism 545 as illustrated in FIG. 5B.

708: Sensing biometric data of the user using a biometric sensor, such as a fingerprint sensor 650 illustrated in FIG. 6A or iris scan sensor 655 illustrated in FIG. 6B.

712: The process may include determining whether an identity of the user is recognized based on the sensed biometric data for the user.

716: If an identity of a user is recognized, then the process may include retrieving data from the identified user from a local or remote storage.

718: Setting strap adjustment thresholds based at least in part on the retrieved user data.

724: The process may proceed with receiving sensor data from the pressure sensors.

728: Automatically adjusting the straps of the harness, including tightening/loosening or inflating/deflating the straps, based on the sensor data until one or more thresholds are met, wherein automatically adjusting the straps of the HMD may include a microcontroller controlling operation of a motor rolling mechanism 430 as illustrated in FIG. 4A or 437 illustrated in FIG. 4B, or a pump mechanism 545 as illustrated in FIG. 5B.

732: Subsequent to the automatic adjustment of the straps 720 or 728, the process may further include adjusting the straps further in response to manual user input, wherein the manual user input may be fine tuning of the strap fit.

736: Storing user data, including data regarding the fine tuning of the strap fit, in a local or remote storage.

740: Readjustment of the straps upon detection of a change in sensor data, such as a change in pressure sensor data.

744: Releasing strap tension upon receiving a command indicating that the user session with the HMD is complete, which may include a command in response to a user pushing a button or otherwise indicating an intention to end a user session.

In the description above, for the purposes of explanation, numerous specific details are set forth in order to provide a thorough understanding of the described embodiments. It will be apparent, however, to one skilled in the art that embodiments may be practiced without some of these specific details. In other instances, well-known structures and devices are shown in block diagram form. There may be intermediate structure between illustrated components. The components described or illustrated herein may have additional inputs or outputs that are not illustrated or described.

Various embodiments may include various processes. These processes may be performed by hardware components or may be embodied in computer program or machine-executable instructions, which may be used to cause a general-purpose or special-purpose processor or logic circuits programmed with the instructions to perform the processes. Alternatively, the processes may be performed by a combination of hardware and software.

Portions of various embodiments may be provided as a computer program product, which may include a computer-readable medium having stored thereon computer program instructions, which may be used to program a computer (or other electronic devices) for execution by one or more processors to perform a process according to certain embodiments. The computer-readable medium may include, but is not limited to, magnetic disks, optical disks, read-only memory (ROM), random access memory (RAM), erasable programmable read-only memory (EPROM), electrically-erasable programmable read-only memory (EEPROM), magnetic or optical cards, flash memory, or other type of computer-readable medium suitable for storing electronic instructions. Moreover, embodiments may also be downloaded as a computer program product, wherein the program may be transferred from a remote computer to a requesting computer.

Many of the methods are described in their most basic form, but processes can be added to or deleted from any of the methods and information can be added or subtracted from any of the described messages without departing from the basic scope of the present embodiments. It will be apparent to those skilled in the art that many further modifications and adaptations can be made. The particular embodiments are not provided to limit the concept but to illustrate it. The scope of the embodiments is not to be determined by the specific examples provided above but only by the claims below.

If it is said that an element "A" is coupled to or with element "B," element A may be directly coupled to element B or be indirectly coupled through, for example, element C. When the specification or claims state that a component, feature, structure, process, or characteristic A "causes" a component, feature, structure, process, or characteristic B, it means that "A" is at least a partial cause of "B" but that there may also be at least one other component, feature, structure, process, or characteristic that assists in causing "B." If the specification indicates that a component, feature, structure, process, or characteristic "may", "might", or "could" be included, that particular component, feature, structure, process, or characteristic is not required to be included. If the specification or claim refers to "a" or "an" element, this does not mean there is only one of the described elements.

An embodiment is an implementation or example. Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances of "an embodiment," "one embodiment," or "some embodiments" are not necessarily all referring to the same embodiments. It should be appreciated that in the foregoing description of exemplary embodiments, various features are sometimes grouped together in a single embodiment, figure, or description thereof for the purpose of streamlining the disclosure and aiding in the understanding of one or more of the various novel aspects. This method of disclosure, however, is not to be interpreted as reflecting an intention that the claimed embodiments requires more features than are expressly recited in each claim. Rather, as the following claims reflect, novel aspects lie in less than all features of a single foregoing disclosed embodiment. Thus, the claims are hereby expressly incorporated into this description, with each claim standing on its own as a separate embodiment.

In some embodiments, a head mounted display apparatus includes a display unit; a strap harness including one or more straps; one or more pressure sensors; a microcontroller; and one or more automatic adjustment mechanisms for the one or more straps, wherein the microcontroller is to adjust the one or more straps by controlling operation of the one or more automatic adjustment mechanisms based at least in part on sensor data from the one or more pressure sensors.

In some embodiments, the one or more pressure sensors include one or more pressure sensors to measure a pressure of the apparatus against one or more points of a user's face or head.

In some embodiments, the one or more pressure sensors include one or more pressure sensors embedded in the one or more straps.

In some embodiments, the one or more automatic adjustment mechanisms include one or more motor rolling mechanisms to tighten or loosen one or more straps.

In some embodiments, the one or more automatic adjustment mechanisms include one or more pump mechanisms to inflate more or more inflatable straps.

In some embodiments, the apparatus further includes one or more biometric sensors, the apparatus to identify a user based on sensor data received from the one or more biometric sensors.

In some embodiments, the one or more biometric sensors include a fingerprint sensor to sense a fingerprint of the user of the apparatus.

In some embodiments, the one or more biometric sensors include an iris scan sensor to sense an iris of one or both eyes of the user of the apparatus.

In some embodiments, the apparatus is to save or retrieve user data regarding adjustment of the one or more straps, the user data being stored in a local or remote storage.

In some embodiments, the microcontroller is to readjust the one or more straps during an operation of the apparatus based at least in part on a change in sensor data from the one or more pressure sensors.

In some embodiments, a computer-readable storage medium having stored thereon data representing sequences of instructions that, when executed by one or more processors, cause the one or more processors to perform operations including receiving sensor data from one or more pressure sensors of a head mounted display; and automatically adjusting one or more straps of a harness of the head mounted display based at least in part on the sensor data until one or more thresholds are met, wherein automatically adjusting the one or more straps includes controlling operation of one or more automatic adjustment mechanisms based at least in part on the sensor data from the one or more pressure sensors.

In some embodiments, automatically adjusting the one or more straps includes one or more of adjusting one or more motor rolling mechanisms to tighten or loosen one or more straps or inflating or deflating more or more inflatable straps.

In some embodiments, the instructions further include instructions for initially loosening or tightening the one or more straps for use of the head mounted display by a user.

In some embodiments, the instructions further include instructions for sensing biometric data for a user using a biometric sensor.

In some embodiments, the instructions further include instructions for identifying the user based at least in part on the biometric data.

In some embodiments, the biometric data includes one or more of fingerprint sensor data and iris scan sensor data.

In some embodiments, the instructions further include instructions for storing user data to or retrieving user data from a storage based at least in part on an identity of the user.

In some embodiments, the instructions further include instructions for readjusting the one or more straps during an operation based at least in part on a change in sensor data.

In some embodiments, an apparatus includes means for receiving sensor data from one or more pressure sensors of a head mounted display; and means for automatically adjusting one or more straps of a harness of the head mounted display based at least in part on the sensor data until one or more thresholds are met, wherein automatically adjusting the one or more straps includes controlling operation of one or more automatic adjustment mechanisms based at least in part on the sensor data from the one or more pressure sensors.

In some embodiments, the means for automatically adjusting the one or more straps includes one or more of means for adjusting one or more motor rolling mechanisms to tighten or loosen one or more straps or means for inflating or deflating more or more inflatable straps.

In some embodiments, the apparatus further includes means for initially loosening or tightening the one or more straps for use of the head mounted display by a user.

In some embodiments, the apparatus further includes means for sensing biometric data for a user using a biometric sensor.

In some embodiments, the apparatus further includes means for identifying the user based at least in part on the biometric data.

In some embodiments, the biometric data includes one or more of fingerprint sensor data and iris scan sensor data.

In some embodiments, the apparatus further includes means for storing user data to or retrieving user data from a storage based at least in part on an identity of the user.

In some embodiments, the apparatus further includes means for readjusting the one or more straps during an operation based at least in part on a change in sensor data.

In some embodiments, a system includes a head mounted display including a display unit, a strap harness including one or more straps, one or more pressure sensors, a microcontroller, one or more automatic adjustment mechanisms for the one or more straps, and a wired or wireless transceiver to communicate with one or more external devices; and a central control system including a controller to provide control operations for the head mounted display and a wired or wireless transceiver to communicate with the head mounted display, wherein the microcontroller of the head mounted display is to adjust the one or more straps by controlling operation of the one or more automatic adjustment mechanisms in response to one or more commands from the controller of the central control system, adjustment of the one or more straps being based at least in part on sensor data from the one or more pressure sensors.

In some embodiments, the one or more pressure sensors include one or more pressure sensors to measure a pressure of the head mounted display against one or more points of a user's face or head.

In some embodiments, the one or more pressure sensors include one or more pressure sensors embedded in the one or more straps.

In some embodiments, the one or more automatic adjustment mechanisms include one or more motor rolling mechanisms to tighten or loosen one or more straps.

In some embodiments, the one or more automatic adjustment mechanisms include one or more pump mechanisms to inflate more or more inflatable straps.

What is claimed is:

1. A head mounted display apparatus comprising:
    a display unit;
    a strap harness including one or more straps;
    at least one pressure sensor;
    at least one controller; and
    one or more automatic adjustment mechanisms for the one or more straps, wherein the one or more automatic adjustment mechanisms include one or more motor rolling mechanisms to tighten or loosen one or more of the straps;
    wherein the at least one controller is to adjust the one or more straps by controlling operation of the one or more automatic adjustment mechanisms based at least in part on sensor data from the at least one pressure sensor.

2. The apparatus of claim 1, wherein the at least one pressure sensor is to measure a pressure of the apparatus against one or more points of a face or head of a user.

3. The apparatus of claim 2, wherein one or more of the at least one pressure sensor are embedded in the one or more straps.

4. The apparatus of claim 1, wherein the one or more automatic adjustment mechanisms include one or more pump mechanisms to inflate one or more inflatable straps.

5. The apparatus of claim 1, further including one or more biometric sensors, the at least one controller to identify a user based on sensor data received from the one or more biometric sensors.

6. The apparatus of claim 5, wherein the one or more biometric sensors include a fingerprint sensor to sense a fingerprint of the user.

7. The apparatus of claim 5, wherein the one or more biometric sensors include an iris scan sensor to sense an iris of one or both eyes of the user.

8. The apparatus of claim 1, wherein the at least one controller is to save or retrieve user data regarding adjustment of the one or more straps, the user data being stored in a local or remote storage.

9. The apparatus of claim 1, wherein the at least one controller is to readjust the one or more straps based at least in part on a change in the sensor data from the at least one pressure sensor.

10. A computer-readable storage medium comprising instructions that, when executed, cause one or more processors to
    receive sensor data from one or more pressure sensors of a head mounted display; and
    automatically adjust one or more straps of a harness of the head mounted display based at least in part on the sensor data until one or more thresholds are met, wherein the automatically adjusting of the one or more straps includes adjusting one or more motor rolling mechanisms to tighten or loosen one or more of the straps based at least in part on the sensor data from the one or more pressure sensors.

11. The computer-readable storage medium of claim 10, wherein the instructions cause the one or more processors to initially loosen or tighten the one or more straps for use of the head mounted display by a user.

12. The computer-readable storage medium of claim 10, wherein the instructions cause the one or more processors to determine biometric data for a user based on data from a biometric sensor.

13. The computer-readable storage medium of claim 12, wherein the instructions cause the one or more processors to identify the user based at least in part on the biometric data.

14. The computer-readable storage medium of claim 13, wherein the biometric data includes one or more of fingerprint sensor data and iris scan sensor data.

15. The computer-readable storage medium of claim 13, wherein the instructions cause the one or more processors to store user data to or retrieve user data from a storage based at least in part on an identity of the user.

16. The computer-readable storage medium of claim 10, wherein the instructions cause the one or more processors to readjust the one or more straps based at least in part on a change in the sensor data.

17. A system comprising:
a head mounted display including:
a display unit, a strap harness including one or more straps, one or more pressure sensors, a first controller, one or more automatic adjustment mechanisms for the one or more straps, and at least one transceiver to communicate with one or more external devices, wherein the one or more automatic adjustment mechanisms include one or more motor rolling mechanisms to tighten or loosen one or more of the straps; and a central control system including:
a second controller to provide control operations for the head mounted display and the at least one transceiver to communicate with the head mounted display;
wherein the first controller is to adjust the one or more straps by controlling operation of the one or more automatic adjustment mechanisms in response to one or more commands from the second controller of the central control system, the adjustment of the one or more straps based at least in part on sensor data from the one or more pressure sensors.

18. The system of claim 17, wherein the one or more pressure sensors are to measure a pressure of the head mounted display against one or more points of a face or head of a user.

19. The system of claim 18, wherein at least one of the one or more pressure sensors is embedded in the one or more straps.

20. The system of claim 17, wherein the one or more automatic adjustment mechanisms include one or more pump mechanisms to inflate one or more inflatable straps.

* * * * *